United States Patent [19]

Iijima et al.

[11] Patent Number: 5,080,907
[45] Date of Patent: Jan. 14, 1992

[54] PHARMACEUTICAL PREPARATIONS CONTAINING NON-STEROIDAL ANTI-INFLAMMATORY AGENTS

[75] Inventors: Takeo Iijima, Koushoku; Masaki Otagiri, Kumamoto; Masao Ueno, Tokorozawa; Tetsu Miyoshi, Kawagoe, all of Japan

[73] Assignee: Nisshin Flour Milling Co., Ltd., Tokyo, Japan

[21] Appl. No.: 607,743

[22] Filed: Oct. 29, 1990

Related U.S. Application Data

[63] Continuation of Ser. No. 164,381, Mar. 4, 1988, abandoned.

[30] Foreign Application Priority Data

Mar. 9, 1987 [JP] Japan ................... 62-52054
Feb. 10, 1988 [JP] Japan ................... 63-27791

[51] Int. Cl.⁵ .................. A61K 31/19; A61K 9/26
[52] U.S. Cl. ........................ 424/469; 514/2; 514/21; 514/570; 514/801
[58] Field of Search ............ 514/2, 21, 570, 801; 530/354, 360, 361; 424/469

[56] References Cited

U.S. PATENT DOCUMENTS

| | | | |
|---|---|---|---|
| 4,347,234 | 8/1982 | Wahlig et al. | 424/426 |
| 4,474,766 | 10/1984 | Goldenberg et al. | 424/177 |
| 4,572,832 | 2/1986 | Kigasawa et al. | 514/773 |
| 4,606,909 | 8/1986 | Bechgaard et al. | 424/481 |

FOREIGN PATENT DOCUMENTS 291819 7/1965 Netherlands .

OTHER PUBLICATIONS

Chemical Abstracts, vol. 86, No. 6, 34219u (1977).

*Primary Examiner*—Douglas W. Robinson
*Assistant Examiner*—Jean C. Witz
*Attorney, Agent, or Firm*—Abelman Frayne Rezac & Schwab

[57] ABSTRACT

Pharmaceutical preparations for oral administration are disclosed which comprise (a) an acidic non-steroidal anti-inflammatory agent having the mean particle size of about 100 μm or less and (b) a protein hydrolyzate or a polypeptide having the mean molecular weight of 4000–12000. The pharmaceutical preparations are in the form of tablets, granules, capsules and dry syrups. They achieve high bioavailability of the anti-inflammatory agent, e.g., ibuprofen.

4 Claims, 2 Drawing Sheets

PHARMACEUTICAL PREPARATIONS CONTAINING NON-STEROIDAL ANTI-INFLAMMATORY AGENTS

This application is a continuation of application Ser. No. 164,381, filed Mar. 4, 1988 now abandoned.

FIELD OF THE INVENTION

The present invention relates to pharmaceutical preparations for oral administration which comprise an acidic non-steroidal anti-inflammatory agent (hereinafter called "acidic NSAID").

BACKGROUND OF THE INVENTION

The acidic NSAID possesses various pharmacological activities such as anti-inflammatory, analgesic and antipyretic activities. Immediate effect is desired for achieving the analgesic and anti-pyretic activities soon after the oral preparation has been administered Of the preparations administered orally, tablets are most suited in view of compliance by patients, and hence, tablets comprising the acidic NSAID, which is absorbed rapidly, are desired.

Injectable preparations, such as ketoprofen subcutaneous injectable preparation and aspirin D-lysinate intravenous injectable preparation, have been developed so far in order to achieve quicker emergence of effects than do the preparations for oral administration.

However, while injectable preparations may achieve the immediate effects, their application is limited due to the mode of administration. Moreover, they can cause troubles such as constriction of quadriceps femoris muscle liable to such side effects as fibrosis of muscle tissues.

Under these circumstances, preparations for oral administration, containing an acidic NSAID, that may be absorbed quickly and that have decreased side effects are wanted.

In general, the acidic NSAID is sparingly soluble in water at a pH range of from acidic to weak acidic, if they are in the crystalline state. Therefore, absorption of the acidic NSAID tends to be delayed or decreased at the upper small intestine, when they are administered in the crystalline state.

Meanwhile, the acidic NSAID tends to cause gastric disorders, when they are administered orally in a dissolved state, as they are absorbed from the stomach in the non-ionic form by the influence of pH in the stomach.

From the above standpoints of view, it is considered to be a problem to be solved to prepare acidic NSAID preparations that pass the stomach in the crystalline state and that dissolve quickly at a region from the outlet of the stomach to the inlet of the small intestine, in order to develop acidic NSAID preparations having the immediate analgesic and anti-pyretic effects and having the decreased side effects.

Thus, we aimed at the relationship between the solubility of the acidic NSAID and the pH of the site at which they are absorbed. Namely, we tried to improve the solubility of the acidic NSAID in the crystalline state at a pH region of 5.8-6.5 and to elucidate substances that can mask the acid moiety of the acidic NSAID. This was in pursuit of substances whereby oral preparations may be obtained to achieve a high absorption rate, a high bioavailability (AUC or the integral of blood concentration curve) and a reduced irritation upon administration.

As a result, we have found that certain protein hydrolyzates such as hydrolyzate of gelatin or casein, or polypeptides possess the above-mentioned properties, leading to the completion of the present invention.

SUMMARY OF THE INVENTION

An object of the present invention is to provide solid preparations containing an acidic NSAID which are of the advantages in the production and distribution, good portability, easy and accurate dosage and method of administration, quick absorption and high bioavailability..

Another object of the invention is to provide a dry syrup which can easily form a uniform suspension when shaken together with water, has a good storage property and can be orally administered without giving any unpleasant sourness and bitterness.

Other objects of the invention will be obvious from the contents of the specification hereinafter disclosed.

DETAILED DESCRIPTION OF THE INVENTION

Figure 1:
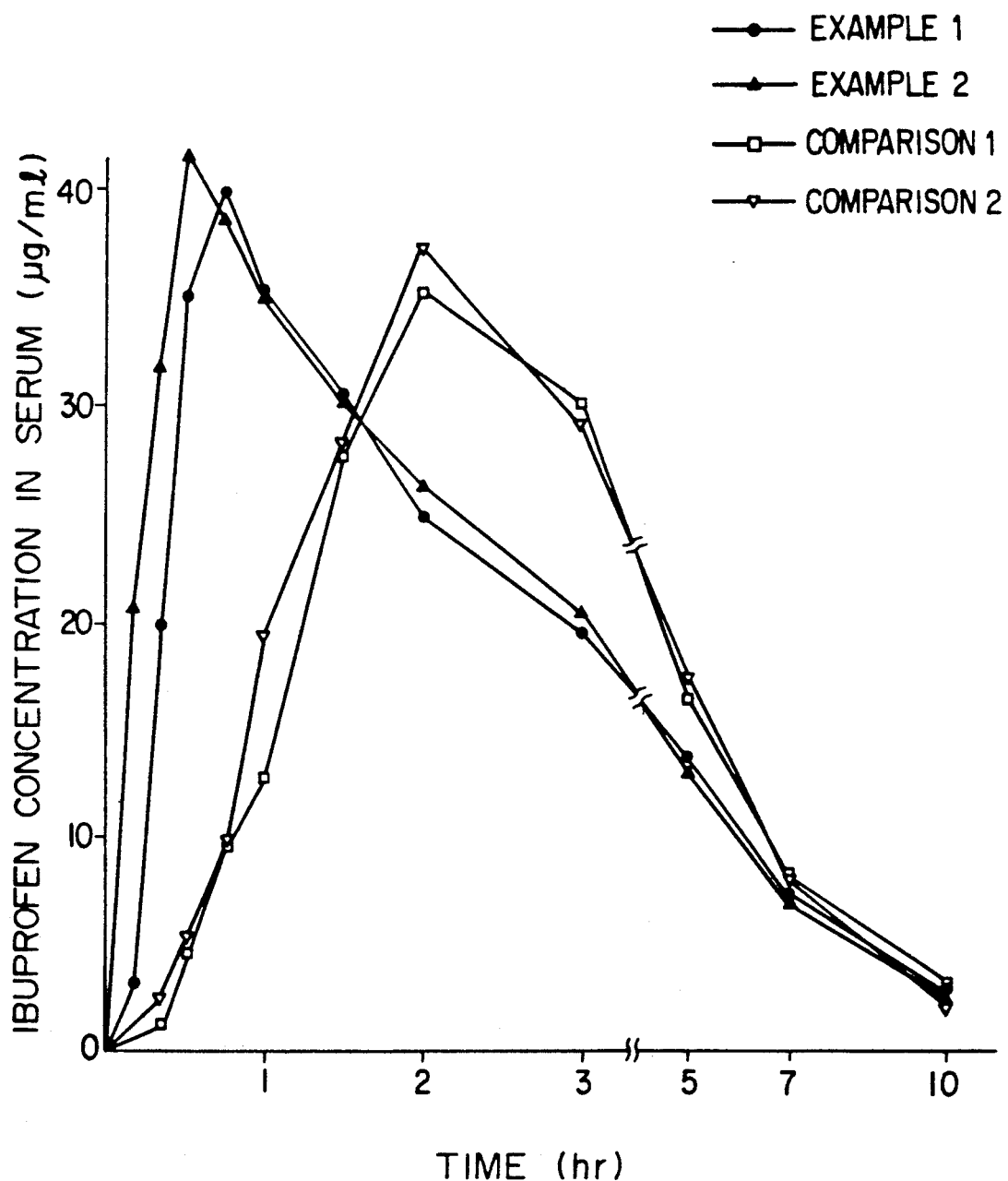
FIG. 1 is a graph showing the chronological changes of ibuprofen concentrations in sera when the ibuprofen solid preparations were administered orally to the dogs.

According to the present invention, there are provided pharmaceutical preparations for oral administration which comprise (a) an acidic non-steroidal anti-inflammatory agent having the mean particle size of about 100$\mu$m or less, and (b) a protein hydrolyzate or a polypeptide having the mean molecular weight of 4000-12000.

The amount of the protein hydrolyzate or polypeptide in the preparation for oral administration according to the present invention is preferably from 0.1 to 10 times by weight based on the acidic NSAID. However, the amount may be changed depending on various factors such as the nature of the pharmaceuticals (active ingredients) and method of preparation. The component (b) may exhibit the desired effect even when it is used in a smaller amount.

The preparations for oral administration of this invention may contain, besides the components (a) and (b) mentioned above, various auxiliary agents known in the art, such as excipients, disintegrating agents, lubricants or the like.

The acidic NSAID to be employed in the present invention as the active ingredient may include, for example, non-steroidal anti-inflammatory agents of phenylpropionic acid series such as ibuprofen, ketoprofen, naproxen, tolmetin, furabiprofen or alclofenac, non-steroidal anti-inflammatory agents of salicylic acid series such as aspirin, non-steroidal anti-inflammatory agents of anthranilic acid series such as mefenamic acid or flufenamic acid, or indomethacin.

The acidic NSAID may be pulverized by wet method or dry method, using a suitable pulverizer. They should be pulverized to a mean particle size of 100 $\mu$m or less, preferably 50 $\mu$m or less, and most preferably 10$\mu$m or less, to ensure the desired solubility.

The present invention is characterized by the protein hydrolyzate or polypeptide as the protective colloidal substance that is charged positively and that covers the surface of the acidic NSAID particles which is the active principle and which is charged negatively. The protein hydrolyzate includes, for example, hydolyzates of gelatin and of casein. Of these, the hydrolyzate of gelatin is most suitable in view of productivity and availability. The hydrolyzate of gelatin may be prepared by an enzymatic degradation of gelatin or any material containing gelatin with a proteolytic enzyme. The mean molecular weight of such hydrolyzate is in the range of 4000-12000, preferably 5500-5500.

The hydrolyzate of casein having a similar structure to that of gelatin may be obtained by hydrolysis of a protein of plant or animal origin with a proteolytic enzyme and contains in its structure free carboxylic and amino groups. Polypeptides include, for example, polypepton.

The form of preparations according to the present invention should most preferably be tablets in view of compliance by patients. However, capsules, granules or other suitable preparations may equally be employed from the aspects of improvements in the immediate effect and bioavailability.

In manufacturing the acidic NSAID preparation of the invention, it is preferable to use a method whereby the component (b), e.g. the hydrolyzate of gelatin may be dispersed more uniformly in the composition and come into close contact with the active ingredient. For this purpose, wet granulation methods, such as the kneading method in which the composition is kneaded with water or a suitable solvent, dried, shifted and tableted, or the semi-direct compression method in which the active ingredient and a component (b), e.g. the hydrolyzate of gelatin are kneaded, dried, shifted, mixed with various additives and then tableted are preferred. However, dry methods may equally be used by adjusting the amount of the component (b) such as the hydrolyzate of gelatin.

The wet methods are preferable also for manufacturing granules and capsules. Here again, however, the dry methods may equally be employed.

The preparations such as tablets and granules may be subjected to gastric soluble film coating for the purpose of masking, etc.

The another form of preparations according to the present invention may be a dry syrup. The dry syrup comprises, based on the weight of the preparations, (a) 5 to 40%, preferably 10 to 40%, most preferably 20 to 30% by weight of an acidic non-steroidal anti-inflammatory agent having the mean particle size of about 100μm or less, (b) 5 to 50%, preferably 20 to 50%, most preferably 20 to 40% by weight of a protein hydrolyzate or a polypeptide having the mean molecular weight of 4000 to 12000, (c) 10 to 40%, preferably 10 to 30% by weight of saccharides, (d) 0 to 30%, preferably 10 to 20% by weight of a suspending and stabilizing agent and (e) 0 to 15%, preferably 3 to 10% by weight of a surface active agent having the HLB value of 10 or higher. The suspension prepared by adding water to the dry syrup can be taken without any unpleasant sourness and bitterness peculiar to the acidic NSAID. The dry syrup may contain additionally fungicides such as sorbic acid, and further various auxiliary agents known in the art such as correctives, solubilizing agents, stabilizers, coloring matters and the like.

A surface active agent is employed in order to accelerate the dispersion rate when water is added and may be any of those agents which have usually the HLB value of 10 or higher, preferably of 12 to 18, are solid at room temperature and are commonly used for foods and drugs. Sucrose aliphatic acid esters are particularly suitable for this purpose.

The suspending and stabilizing agents include, for example, Aerosil (trade name of Nippon Aerosil K.K.), Carplex (trade name of Shionogi Pharmaceutical Co., Ltd.), JP light anhydrous silicic acid or silicon oxide, silica gel, talc or calcium carbonate, etc., the average particle size thereof being not more than approximately 50 μm.

The saccharides which may be employed in the invention include, for example, sucrose (JP), sucrose, fine granulated sugar, glucose, raffinose, sorbitol, fructose, dextrin, etc., with sucrose (JP), sucrose and sorbitol being preferable.

The preparations for oral administration according to the present invention are distinguished over the prior art preparations by the greater absorption rate with less variation by individuals, by quicker emergence of effect and better bioavailability with an equivalent integral of blood concentration curve.

The present invention will be explained in more detail by the following Examples, which are presented merely for illustrative purpose and should not be construed to limit the scope of the invention.

EXAMPLE 1

|  | Weight % |
|---|---|
| Ibuprofen | 40 |
| (mean particle size 12 μm) | |
| Hydrolyzate of gelatin | 12 |
| (mean molecular weight 6,800) | |
| Perfiller 101 | 27 |
| Carboxymethyl cellulose | 20 |
| Magnesium stearate | 1 |
|  | 100 |

Of the above components, ibuprofen, hydrolyzate of gelatin and Perfiller 101 (20% synthetic aluminum silicate, 60% hydroxypropyl starch, 20% crystalline cellulose, manufactured by Freund Ind., Co., Ltd.) were kneaded with water, granulated, dried and shifted The shifted granules were mixed with the corresponding amounts of carboxymethyl cellulose and magnesium stearate The compound was compressed to a diameter 8 mm, applying weight of 200 mg per tablet. A gastric soluble coating was effected using a coating agent comprising hydroxypropylmethyl cellulose as the main component to give the desired tablets.

EXAMPLE 2

Of the components described in Example 1, ibuprofen, hydrolyzate of gelatin and Perfiller 101 and carboxymethyl cellulose were kneaded with water, granulated, dried and shifted through a screen of 20-32 mesh. The shifted granules were mixed with the corresponding amount of magnesium stearate and the compound was blended to give the desired granules.

EXAMPLE 3

|  | Weight % |
|---|---|
| Ibuprofen | 27 |
| (mean particle size 10 μm or less) | |
| Hydrolyzate of gelatin | 27 |
| (mean molecular weight 6,800) | |
| Refined sugar | 27 |

| | Weight % |
|---|---|
| Light silicic acid anhydride | 13 |
| Ryoto sugar ester (sucrose fatty acid ester, Mitsubishi Kasei Shokuhin KK) | 6 |
| | 100 |

The refined sugar was pulverized, and then mixed with the prescribed amounts of hydrolyzate of gelatin, light silicic acid anhydride and Ryoto sugar ester. The compound was thoroughly blended and pulverized and then mixed with previously pulverized ibuprofen. The whole mixture was throughly blended and filled in empty capsules to give the desired capsules.

COMPARISON 1

| | Weight % |
|---|---|
| Ibuprofen (mean particle size 90 μm) | 40 |
| Lactose | 10.5 |
| Perfiller 101 | 27 |
| Carboxymethyl cellulose | 20 |
| Light silicic acid anhydride | 1.5 |
| Magnesium stearate | 1 |
| | 100 |

The above ingredients were weighed out, mixed and tableted to diameter 8 mm, applying weight of 200 mg per tablet. The tablets were then subjected to gastric soluble coating as in Example 1, to give the desired tablets.

COMPARISON 2

| | Weight % |
|---|---|
| Ibuprofen (mean particle size 110 μm) | 40 |
| Hydrolyzate of gelatin (mean molecular weight 6,800) | 12 |
| Perfiller 101 | 27 |
| Carboxymethyl cellulose | 20 |
| Magnesium stearate | 1 |
| | 100 |

Tablets were prepared using the composition described above and following the procedure described in Example 1.

EXAMPLE 4

| | Weight % |
|---|---|
| Ibuprofen (particle size of 10 μm or less) | 27.03 |
| Gelatin hydrolyzate (average molecular weight of 6,800) | 27.03 |
| Sucrose (JP) | 27.03 |
| Light anhydrous silicic acid | 13.51 |
| Ryoto Sugar Ester | 5.40 |
| | 100 |

The refined sugar was pulverized, and then mixed with the prescribed amounts of hydrolyzate of gelatin, light silicic acid anhydride and Ryoto sugar ester. The compound was thoroughly blended and pulverized and then mixed with previously pulverized ibuprofen. The whole mixture was thoroughly blended to prepare uniform powders.

EXAMPLE 5

Following the same formulation and procedure as in Example 4 but using the ibuprofen having the average particular size of 100 μm, there was prepared the composition.

COMPARISON 3

Ibuprofen powder (average particle size of 100 μm).

COMPARISON 4

Ibuprofen powder (particle size of 10 μm or less)

COMPARISON 5

An aqueous ibuprofen solution at 20 mg/ml was prepared by adding a NaOH solution having the same concentration as ibuprofen and then adjusted to the pH value of 7 with 0.1N HCL.

COMPARISON 6

| | Weight % |
|---|---|
| Ibuprofen (particle size of 10 μm or less) | 2.44 |
| Hydroxypropyl methyl cellulose (2% aqueous solution) | 54.10 |
| Refined sugar | 27.10 |
| Purified water | 16.26 |
| | 100 |

The ibuprofen was taken in the prescribed amount and a 2% aqueous solution of hydroxypropyl methyl cellulose in the prescribed amount was added portionwise, with stirring well. To the resulting mixture was added the refined sugar in the prescribed amount previously prepared in purified water and the resulting mixture was further stirred to a homogeneous suspension.

COMPARISON 7

Following the same formulation and procedure as in Comparison 6 but using ibuprofen with the average particle size of 100 μm, there was prepared a syrup.

ADMINISTRATION TEST

Each of the preparations prepared in Examples 1 to 5 and Comparisons 1 to 7 was administered orally to five beagles by the crossover method and then the blood concentrations of ibuprofen were measured chronologically. The oral administration was made in such a way that 80 mg equivalent of ibuprofen was administered to a beagle with 20 ml of water. The results are shown in Tables 1 and 2 as well as FIGS. 1 and 2.

As shown in Table 1 and FIG. 1, the time required to reach the maximum blood concentration (Tmax) is significantly shorter with the preparations of Examples 1 and 2 than that with the preparations of Comparisons 1 and 2. Moreover, increase in the maximum blood concentration (Cmax) was observed with the preparations of Examples 1 and 2.

In Tables 1 and 2, each figure is the mean value of ibuprofen concentrations (μg/ml) in sera of 5 beagles.

Figure 2:
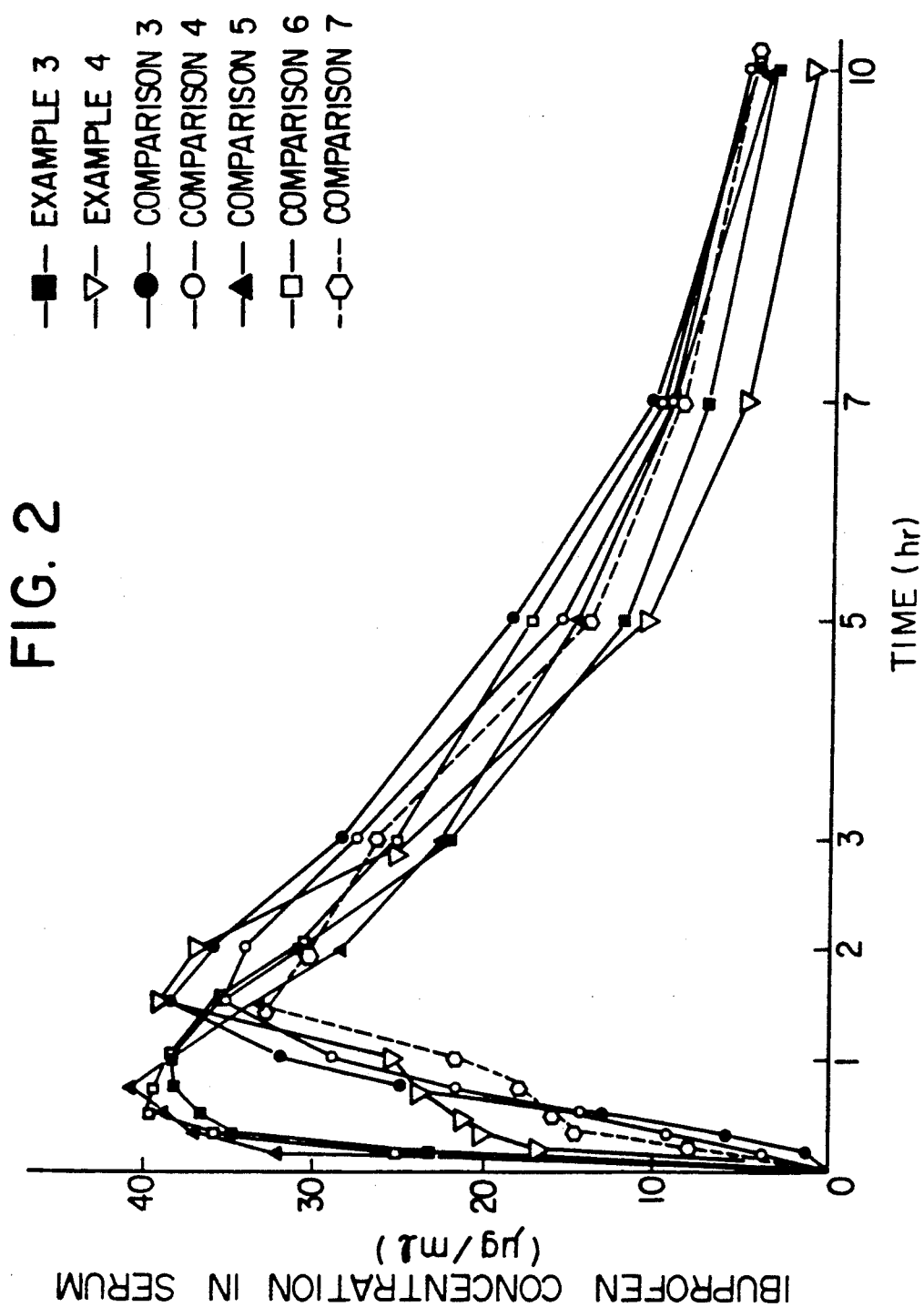
FIG. 2 is a graph showing the chronological changes of ibuprofen concentrations in sera when the ibuprofen preparations were administered orally to the dogs.

As shown in Table 2 and FIG. 2, Examples 4 and 5 show a similar blood concentration pattern to Comparisons 5 and 6, and further show a significantly rapid absorption.

The preparations of Comparisons 6 and 7 were used as they are, while for those of Examples 4 and 5, each 400 mg was dissolved in 5.4 ml of water and 4 ml of a resulting solution was used for administration. IN Comparison 5, a 20 mg solution of ibuprofen was used in the amount of 4 ml and the solution was administered by syringe to the depth of throat. In Comparisons 3 and 4, and powders filled in a No. 2 hard capsule were administered.

TABLE 1

Change of concentration in serum ($\mu$g/ml) after administration

| Example | Time (minutes) | | | | | | | | | | |
|---|---|---|---|---|---|---|---|---|---|---|---|
| | 10 | 20 | 30 | 45 | 60 | 90 | 120 | 180 | 300 | 420 | 600 |
| Example 1 | 3.11 | 19.85 | 35.14 | 40.42 | 35.43 | 30.46 | 24.93 | 19.62 | 13.57 | 7.13 | 2.75 |
| Example 2 | 20.81 | 31.92 | 41.83 | 38.84 | 35.37 | 30.34 | 26.39 | 20.51 | 13.04 | 6.88 | 2.60 |
| Comparison 1 | 0.62 | 1.25 | 4.61 | 9.42 | 12.85 | 27.64 | 35.60 | 30.26 | 16.11 | 7.96 | 3.07 |
| Comparison 2 | 0.75 | 2.36 | 5.21 | 9.60 | 19.37 | 28.25 | 37.36 | 29.24 | 17.19 | 7.89 | 2.13 |

TABLE 2

Change of concentration in serum ($\mu$g/ml) after administration

| Example | Time (minutes) | | | | | | | | | | |
|---|---|---|---|---|---|---|---|---|---|---|---|
| | 10 | 20 | 30 | 45 | 60 | 90 | 120 | 180 | 300 | 420 | 600 |
| Example 3 | 23.20 | 34.74 | 36.53 | 38.20 | 38.45 | 35.48 | 30.85 | 22.01 | 12.09 | 7.32 | 3.83 |
| Example 4 | 16.86 | 20.40 | 21.36 | 23.95 | 25.81 | 39.20 | 36.61 | 25.27 | 10.80 | 5.03 | 1.59 |
| Comparison 3 | 1.16 | 5.86 | 13.10 | 24.76 | 31.84 | 38.42 | 35.70 | 28.35 | 18.51 | 10.36 | 4.55 |
| Comparison 4 | 3.79 | 9.26 | 14.40 | 21.55 | 28.81 | 35.14 | 33.84 | 27.47 | 15.60 | 9.36 | 5.15 |
| Comparison 5 | 32.02 | 37.03 | 38.76 | 40.92 | 38.37 | 33.24 | 28.44 | 22.72 | 14.79 | 9.36 | 4.05 |
| Comparison 6 | 25.11 | 35.86 | 39.74 | 39.48 | 38.43 | 35.49 | 30.64 | 25.13 | 17.34 | 9.93 | 4.54 |
| Comparison 7 | 8.04 | 14.51 | 15.78 | 17.89 | 21.44 | 33.11 | 30.19 | 26.29 | 14.04 | 9.14 | 4.71 |

The syrups of Example 3 and Comparison 6 were tested for their suspension stability at room temperature. The results are shown in Table 3.

TABLE 3

| | Lapsed time | | | |
|---|---|---|---|---|
| | 0.5 hour | 3 days | 4 days | 58 days |
| Example 4 | | | | |
| Separation or sedimentation | — | — | — | + + |
| Redispersibility | ○ | ○ | ○ | ○ |
| Comparison 6 | | | | |
| Separation or sedimentation | — | — | — | + |
| Redispersibility | ○ | ○ | ○ | ○ |

+ +: Separation or sedimentation occurred
+: Only slight separation or sedimentation occurred
—: No separation or sedimentation occurred
○: Good redispersibility
x: Difficult to be redispersed In this test, the syrup of Comparison 6 was used as prepared, while the syrup of Example 3 was used after about 370 mg were taken and shaken well with about 5 ml of water. In addition, the dry syrup of Example 3 and the ibuprofen powder of Comparison 4 were evaluated for taste when orally administered. More specifically, a panel was formed by 10 candidates and sourness, bitterness, irritantness and sweetness were respectively evaluated by sensory test. A total of ratings with regard to each evaluation is shown in Table 4.

TABLE 4

| | Example 3 | Control 4 |
|---|---|---|
| Sourness | 0 | 20 |
| Bitterness | 9 | 26 |
| Irritantness | 7 | 26 |
| Sweetness | 6 | 0 |

The ratings for each evaluation in Table 4 are based on the following items.

| | |
|---|---|
| Very strong | 3 |
| Felt | 2 |
| Slightly felt | 1 |
| None | 0 |

Further, the suspension of Comparison 6 was rated for taste when orally administered and had sweetness and irritant bitterness.

What is claimed is:

1. A pharmaceutical preparation in tablet form for oral administration which comprises an acidic non-steroidal anti-inflammatory agent of the phenylpropionic acid series having a mean particle size of about 100 $\mu$m or less and a gelatin hydrolyzate having a means molecular weight of 5500–7500.

2. A pharmaceutical preparation of claim 1 which further comprises conventional pharmaceutical excipients.

3. A pharmaceutical preparation of claim 1 wherein the acidic non-steroidal anti-inflammatory agent is selected from the group consisting of ibuprofen, ketoprofen, naproxen, tolmetin, furabiprofen and alclofenac.

4. A pharmaceutical preparation of claim 1 wherein gelatin hydrolyzate is present in an amount by weight of form 0.1 to 10 times the amount of the acidic non-steroidal anti-inflammatory agent.

* * * * *